United States Patent

Scholl et al.

[11] Patent Number: 6,140,427
[45] Date of Patent: Oct. 31, 2000

[54] VULCANIZATION ACCELERATORS SUITABLE FOR THE INTRODUCTION OF POLAR SUBSTITUENTS

[75] Inventors: Thomas Scholl, Bergisch Gladbach; Hermann-Josef Weidenhaupt, Noervenich; Stefan Kelbch, Odenthal-Erberich; Hans-Wilhelm Engels, Kerpen, all of Germany

[73] Assignee: Bayer AG, Leverkusen, Germany

[21] Appl. No.: 08/124,617

[22] Filed: Sep. 22, 1993

[30] Foreign Application Priority Data

Oct. 2, 1992 [DE] Germany ............... 42 33 197

[51] Int. Cl.⁷ .................................................. C08C 19/20
[52] U.S. Cl. .................... 525/329.3; 525/332.6; 525/332.7; 525/349
[58] Field of Search ............... 525/329.3, 330.4, 525/331.1, 331.8, 332.7, 332.6

[56] References Cited

U.S. PATENT DOCUMENTS 2,026,863  1/1936  Bögemann .
2,510,893  6/1950  Kleiman .
3,770,707  11/1973  Boustany ................. 525/349
4,258,193  3/1981  Fujii ......................... 546/281

FOREIGN PATENT DOCUMENTS 2 430 943  2/1980  France .

OTHER PUBLICATIONS

J. Org. Chem., 47:765 (1982).

*Primary Examiner*—Christopher Henderson
*Attorney, Agent, or Firm*—Connolly Bove Lodge & Hutz LLP

[57] ABSTRACT

New vulcanization accelerators, corresponding to the formula

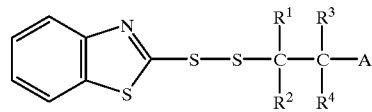

are particularly suitable for the production of vulcanized rubbers modified with lateral polar groups.

8 Claims, No Drawings

VULCANIZATION ACCELERATORS SUITABLE FOR THE INTRODUCTION OF POLAR SUBSTITUENTS

FIELD OF THE INVENTION

The present invention relates to new vulcanization accelerators suitable for the introduction of polar substituents, and to the use of the new vulcanization accelerators for the production of vulcanized rubbers modified with lateral polar groups.

BACKGROUND AND PRIOR ART

The production of vulcanized rubbers modified with lateral polar groups (e.g. OH groups) is known from DE-OS 2 653 144 and from European Patent Application 464 478, for example. According to the above-mentioned patent publications, vulcanized rubbers modified by means of mercaptans such as 2-mercapto-ethanol and thioglycollic acid have better mechanical properties, particularly when containing hydrated silica as a filler, than unmodified vulcanized rubbers containing hydrated silica as a filler. A disadvantage of the processes known from the above-mentioned publications for the production of modified vulcanized rubbers is that the production of modified rubbers and the vulcanization thereof have to be carried out in two separate process steps, which has a significant adverse effect on the process economics.

In addition, organosilanes with a special structure are known from DE-OS 2 255 577, which serve as additives for rubber compounds containing silicate fillers and which have a favourable effect on the properties of the vulcanized materials, in a surprising and definitive manner. The additives described in DE-OS 2 255 577 exert no accelerating effect whatsoever on the vulcanization process; rather, additional amounts of a vulcanization accelerator are necessary to obtain the kinetics and density of cross-linking which are suitable for practical application.

Finally, the production and kinetic behaviour of asymmetric disulphides in vulcanized rubbers are described in Rubber Chem. Technol. 46 (5), pages 1299–1315. The compounds cited therein, such as cyclohexyl-dithiobenzthiazole, contain a cyclohexyl radical, which is non-polar and which is thus not capable of interacting with fillers. Separate tests have shown that these compounds are intrinsically unsuitable for use in vulcanization, on account of their low reactivity and disagreeable odours.

SUMMARY OF THE INVENTION

The present invention accordingly relates to new vulcanization accelerators corresponding to the formula

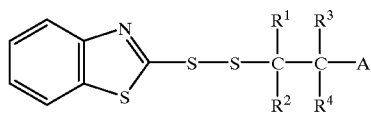

where A represents OH, $OCOR^5$, $OR^5$, $COOR^5$, $NR^6R^7$ or CN, wherein $R^5$, $R^6$ and $R^7$ are the same or different and represent hydrogen, or $C_1$–$C_{12}$ alkyl or $C_6$–$C_{10}$ aryl radicals, and $R_1$ to $R^4$ are the same or different and represent H, $C_1$–$C_{12}$ alkyl, $C_6$–$C_{10}$ aryl, $CH_2OR^5$, $CH_2COOR^5$ and $CH_2OH$, or wherein the $R^1$, $R^2$, $R^3$ and $R^4$ radicals are bonded to one or more carbocyclic rings with 3 to 7 C atoms.

DESCRIPTION OF PREFERRED EMBODIMENTS

The preferred $C_1$–$C_{12}$ alkyl radicals in the above formula comprise methyl, ethyl, propyl, butyl, cyclohexyl, octyl and dodecyl radicals. The preferred $C_6$–$C_{10}$ aryl radicals comprise phenyl and naphthyl radicals. The alkyl and aryl radicals may optionally contain further single or multiple hydroxy or carboxyalkyl substituents, such as methoxy or ethoxy radicals.

The preferred new vulcanization accelerators are those corresponding to the following formulae:

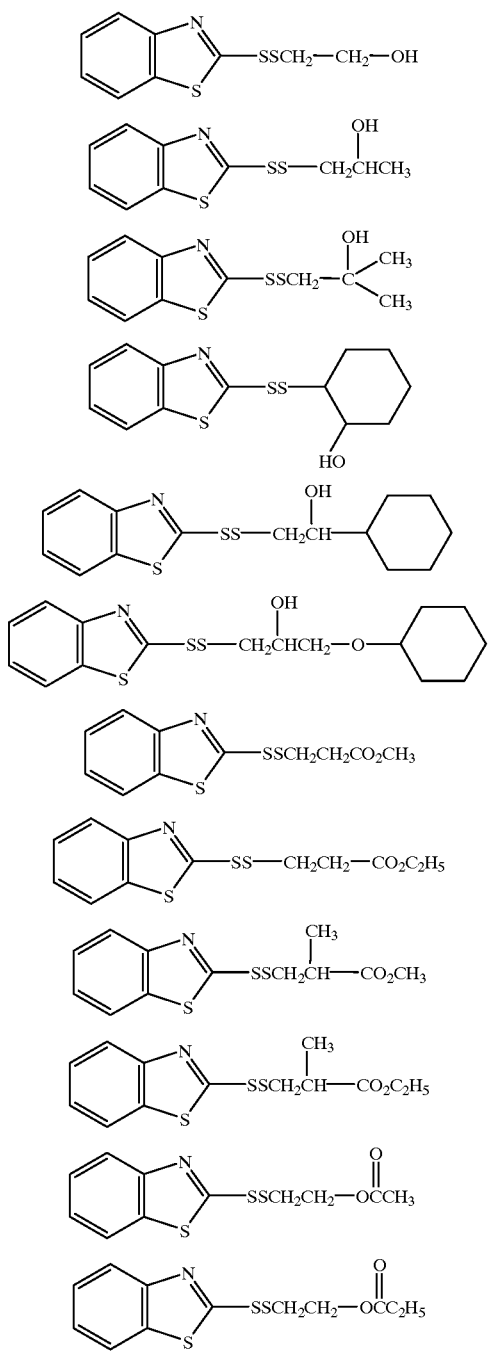

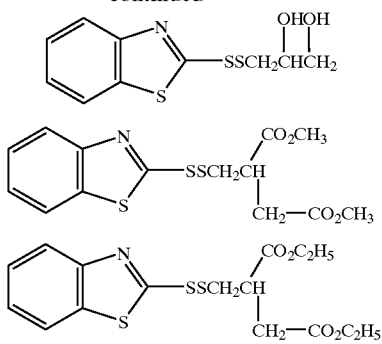

The new vulcanization accelerators are added before vulcanization, in amounts of 0.1 to 10 weight %, preferably 0.3 to 4 weight %, based on the rubber of the rubber compound.

As already stated, the vulcanization accelerators according to the invention are capable of transferring the side-chain

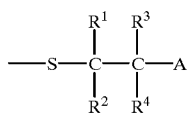

to the rubber polymer during vulcanization, and are thus capable of bringing about a modification of the polymer chain with polar substituents.

In principle, the new vulcanization accelerators may be prepared by three routes:

1. The reaction of mercaptobenzthiazole-sulphene chlorides with appropriately substituted mercaptans, according to reaction scheme A:

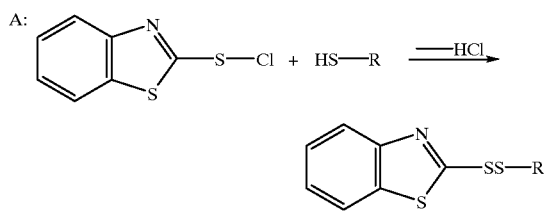

The reaction is preferably carried out within the temperature range from -20 to +50° C., optionally in the presence of bases to react with the hydrogen chloride liberated. Reactions of this type have been described, for example, in Houben-Weyl, Methoden der Organischen Chemie, Thieme Verlag, Stuttgart, Volume E 11, pages 140–142 (1985).

2. From thioimides, by reaction with appropriately substituted mercaptans according to reaction scheme B:

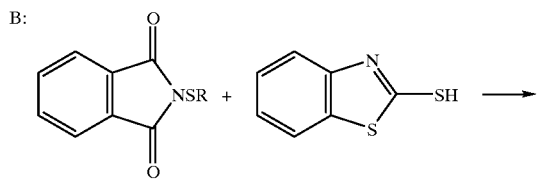

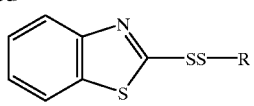

The reactions are preferably carried out at temperatures from 60 to 120° C., and in aromatic solvents. Reactions of this type are described, for example, in Tetrahedron Letters 41 (1970), 3551–3554.

3. By the reaction of 2,2'-dithiobenzthiazole with mercaptans, preferably in the presence of catalytically-active bases and in aprotic solvents at temperatures from 50 to 130° C., according to reaction scheme C:

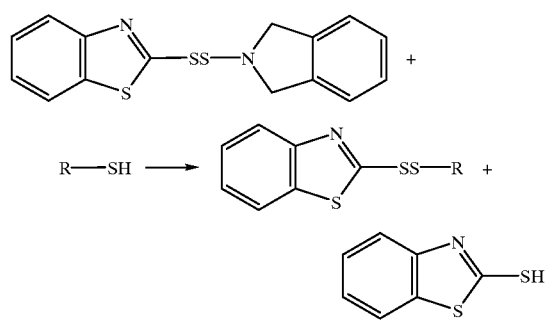

Reactions of this type are described, for example, in Houben-Weyl, Methoden der Organischen Chemie, Thieme Verlag, Stuttgart, Volume E 11, page 146 (1985).

The new vulcanization accelerators are suitable for the vulcanization of both natural rubber and synthetic rubbers. Suitable synthetic rubbers are those described, for example, by W. Hoffmann, Kautschuk-Technologie, Gentner-Verlag, Stuttgart 1980. They comprise, for example, polybutadiene (BR), butadiene/acrylic ester-Cl-$_4$ alkyl ester copolymers (ABR), polychloroprene (CR), polyisoprene (IR), styrene/butadiene copolymers with styrene contents of 1 to 60 weight %, preferably 20 to 50 weight % (SBR), isobutylene/isoprene copolymers (IIR), butadiene/acrylonitrile copolymers with acrylonitrile contents of 5 to 60 weight %, preferably 10 to 50 weight % (NBR), partially hydrogenated or fully hydrogenated NBR rubbers (HBNR), ethylene/propylenediene copolymers (EPDM) and mixtures of these rubbers.

The new vulcanization accelerators may be added during vulcanization, with other rubber additives, such as additional accelerators, anti-ageing agents, heat stabilizers, light stabilizers, ozone protection agents, processing additives, softeners, tack enhancers, blowing agents, colorants, pigments, waxes, extenders, organic acids, retarders, metal oxides, and activators such as triethanolamine, polyethylene glycol and hexanetriol, which are known to the person skilled in the art in the rubber industry. The rubber additives are added in the usual amounts during the vulcanization of the rubbers.

As stated previously, the new vulcanization accelerators are particularly suitable for the production of vulcanized rubbers which contain silicate fillers. Examples of silicate fillers include: highly-dispersed hydrated silicas, manufactured for example by precipitation from silicate solutions or by flame hydrolysis of silicon halides, and with specific surface areas from 5 to 1000 m$^2$/g, preferably 20 to 400 ie/g (BET surface area) and primary particle sizes from 100 to 400 nm. The hydrated silicas may optionally also be present as mixed oxides with other metal oxides such as the oxides of aluminium, magnesium, calcium, barium, zinc, zirconium or titanium. Synthetic silicates are also suitable, such as aluminium silicate or alkaline earth silicates such as magnesium or calcium silicates, with BET surface areas from 20 to 400 m$^2$/g and primary particle diameters from 10 to 400 nm. Other suitable fillers comprise natural silicates such as kaolin and other naturally occurring hydrated silicas, as well as glass fibres and fibreglass products (mat, strand) or glass microspheres.

In addition to the above-mentioned silicate fillers, the known carbon blacks may also be used. Such carbon blacks, for example, are produced by the flame black, furnace black or gas black process and have BET surface areas from 20 to 200 m$^2$/g, such as SAF, ISAF, IISAF, HAF, FEF or GPF blacks.

The new vulcanization accelerators are particularly suitable for use when carbon black is used in the vulcanization of rubbers in addition to silicate fillers such as hydrated silicas. In a vulcanization process such as this, the ratio of hydrated silica to carbon black may be varied within any desired limits. In tyre manufacture, for example, hydrated silica/carbon black ratios from 1:10 to 1:2 (in parts by weight) are employed.

The vulcanization accelerators according to the invention may be processed using the machines which are customary in the rubber industry, such as mixer rolls, kneaders and calenders.

The vulcanized rubbers produced using the vulcanization accelerators according to the invention are particularly suitable for the manufacture of motor vehicle tyres, seals, drive belts and flexible bellows.

EXAMPLES

A: Preparation of the vulcanization accelerators according to the invention

Example 1

2-hydroxyethyl dithiobenzthiazole

Chlorine gas (17.5 g/0.25 mole) was passed at 0 to 50C into a suspension of 2,2'-dithiobisbenzthiazole (83 g/0.25 mole) in chlorobenzene (600 ml). Mercaptoethanol (39 g/0.5 mole) was then added drop-wise to this solution, followed by stirring for 7 hours at room temperature. The precipitated product was filtered off, mixed with methylene chloride (500 ml) and washed with 5% NaHCO$_3$ solution (500 ml). The organic phase was concentrated by evaporation. A yellowish-brown oil (102 g) was obtained, which crystallised after a short time. m.pt.: 65 to 68° C.

$^1$H NMR (CDCl$_3$): 3.1 ppm: 2 alkyl protons (triplet); 3.9 ppm: 2 alkyl protons (triplet); 4.4 ppm: 1 hydroxyl proton (singlet); 7.3 to 7.9 ppm: 4 aromatic protons (multiplet).

| Elemental analysis: | C | H | N | S |
|---|---|---|---|---|
| Calculated: | 44.4 | 3.7 | 5.8 | 39.5% |
| Found: | 44.4 | 3.7 | 5.6 | 39.1% |

Example 2

2-hydroxypropyl dithiobenzthiazole

Chlorine gas (17.5 g/0.25 mole) was passed at 0 to 5° C. into a suspension of 2,2'-dithiobisbenzthiazole (83 g/0.25 mole) in chlorobenzene (600 ml). 1-mercapto-2-propanol (46 g/0.5 mole) was then added drop-wise to this solution, followed by stirring for 7 hours at room temperature. The precipitated product was filtered off and mixed with methylene chloride (500 ml) and 5% NaHCO$_3$ solution (500 ml). The organic phase was then washed twice with water and concentrated by evaporation. A yellowish-brown oil (94 g) was obtained.

$^1$H NMR (CDCl$_3$): 1.3 ppm: 3 methyl protons (doublet); 2.75 to 3.2 ppm: 2 methylene protons (multiplet); 4.0 to 4.1 ppm: 1 methine proton (multiplet); 4.5 ppm: 1 hydroxyl proton (singlet); 7.2 to 8.0 ppm: 4 aromatic protons (multiplet).

Example 3

2-hydroxy-2'-methylpropyl-dithiobenzthiazole

The same procedure was employed as in Examples 1 and 2. When 2-hydroxy-2'-methylpropane (53 g/0.5 mole) was used as the mercapto compound, a viscous yellowish-brown oil (104 g) was obtained.

$^1$H NMR (CDCl$_3$): 1.4 ppm: 6 methyl protons (singlet); 3.2 ppm:

2 methylene protons (singlet); 3.75 ppm: 1 hydroxyl proton (singlet); 7.3 to 8.0 ppm: 4 aromatic protons (multiplet).

Example 4

2-hydroxy-3-phenoxypropyl-dithiobenzthiazole

The procedure of Examples 1 to 3 was employed, using 2-hydroxy-3-phenoxypropyl mercaptan (92 g/0.5 mole) as the mercapto compound, to obtain 147g of a viscous brown oil.

$^1$H NMR (CDCl$_3$): 3.0 to 3.4 ppm: 2 alkyl protons (multiplet); 4.0 to 4.1 ppm: 2 alkyl protons; 4.2 to 4.4 ppm: 1 alkyl proton (multiplet); 4.6 to 4.9 ppm: 1 hydroxyl proton (broad singlet); 6.8 to 7.9 ppm: 9 aromatic protons (multiplet).

Example 5

2,3-dihydroxypropyl-dithiobenzthiazole

The procedure of Examples 1 to 4 was employed using thioglycerol (54 g/0.5 mole) as the mercapto compound, to obtain 59g of a yellow solid with a m.pt. of 115 to 120° C.

$^1$H NMR (d$_6$-DMSO): 3.0 to 3.8 ppm: 5 alkyl protons (multiplet); 4.7 and 5.1 ppm: 2 hydroxyl protons (broad singlet); 7.3 to 8.1 ppm: 4 aromatic protons (multiplet).

Example 6

β-propionic acid-dithiobenzthiazole methyl ester

Chlorine gas (39 g/0.55 mole) was passed at 0 to 5° C. into a suspension of 2,2'-dithiobisbenzthiazole (166 g/0.5 mole) in dry chlorobenzene (1200 ml). After one hour the excess chlorine was removed by briefly applying the vacuum from a water pump. Mercaptopropionic acid methyl ester (132 g/1.1 mole) was then added drop-wise at −5 to −10° C., followed by passing nitrogen through the reaction mixture and stirring for 8 hours at room temperature. The precipitate which formed was filtered off and mixed with 5% NaHCO$_3$ solution (1 1) and methylene chloride (1 1). The organic phase was washed twice with water and was then concentrated by evaporation under vacuum. A light yellow powder (241 g) was obtained, with a m.pt. of 68 to 70° C.

$^1$H NMR (CDCl$_3$): 2.8 to 2.9 ppm: 2 methylene protons (triplet); 3.1 to 3.3 ppm: 2 methylene protons (triplet); 3.7 ppm: 3 methyl protons; 7.3 to 8.0 ppm: 4 aromatic protons

| Elemental analysis: | C | H | N | S |
|---|---|---|---|---|
| Calculated: | 46.3 | 3.9 | 4.9 | 33.7% |
| Found: | 46.3 | 3.9 | 4.9 | 34.0% |

Example 7

2-acetoxyethyl-dithiobenzthiazole 2-hydroxyethyl-dithiobenzthiazole (60.8 g/0.25 mole; see Example 1) was added to acetic anhydride (25.5 g/0.25 mole) in methylene chloride (500 ml). Triethylamine (25.3 g/0.25 mole) was then added drop-wise, and the mixture was stirred for 6 hours at room temperature. The organic phase was then washed twice with water (about 400 ml each time) and the solvent was removed under the vacuum from a water pump. A yellowish-brown oil (59 g) was obtained.

$^1$H NMR (CDCl$_3$): 2.1 ppm: 3 methyl protons (singlet); 3.2 ppm: 2 methylene protons (triplet); 4.4 ppm: 2 methylene protons (triplet); 7.3 to 8.0 ppm: 4 aromatic protons (multiplet).

B: Investigation of the suitability as vulcanization accelerators

Example 8

Rubber compounds of the composition cited below were prepared in a kneader, at an internal temperature of 140° C. and a rotational speed of 50 rpm. The time of compounding was 5 minutes. Sulphur and accelerator were added at the end, at 50° C. on the roll. Cross-linking, as determined by the cross-linking kinetics, was then effected at 150° C., and was measured by means of a curemeter in accordance with DIN 53 529 over a period of 45 minutes. The parameters measured were the time to the commencement of vulcanization (t-s in minutes), the time to reach 90% of the maximum cross-linking (t-90), and the maximum torque (Fmax in N) at the time of the maximum density of cross-linking.

| Rubber compound: | |
|---|---|
| TSR 5 natural rubber (Malaysian rubber) | 100 pts. wt. |
| N 115 carbon black (Degussa) | 48 pts. wt. |
| Stearic acid | 2 pts. wt. |
| Zinc oxide | 3.5 pts. wt. |
| Antilux 110 (Bayer) ozone-protective wax | 1 pts. wt. |
| Oligomeric trimethyl dihydroquinoline (Vulkanox HS, Bayer) | 1 pts. wt. |
| N-isopropyl-N'-phenyl-p-phenylenediamine (Vulkanox 4010 NA, Bayer) | 1.5 pts. wt. |
| Sulphur | see Table |
| Accelerator | see Table |

The following compounds were also tested for comparison, in addition to the accelerators according to the invention:

Comparison 1: 2,2'-dithio-bisbenzthiazole (Vulkacit DM, Bayer)

Comparison 2: bis-triethyloxysilylpropyl tetrasulphide (DE 2,255,577)

TABLE 1

| Accelerator | Sulphur | t-s | t-90 | Fmax |
|---|---|---|---|---|
| 1.4 phr* Ex.[1] 1 | 1.8 phr | 3.6 | 12.9 | 42.3 |
| 1.4 phr Ex. 2 | 1.8 phr | 4.5 | 13.4 | 42.1 |
| 1.4 phr Ex. 5 | 1.8 phr | | | |
| 1.4 phr Ex. 6 | 1.8 phr | 6.23 | 13.4 | 38.5 |
| 1.4 phr Ex. 7 | 1.8 phr | | | |
| 1.4 phr Comp.[2] 1 | 1.8 phr | 2.5 | 9.2 | 39.7 |
| 1.4 phr Comp. 2 | 1.8 phr | . . . No vulcanization . . . | | |

*parts/100 parts rubber
[1]Example
[2]Comparison

It is clear from the results that the compounds according to the invention have an accelerating effect, in contrast to the comparison compound 2, so that additional accelerators may be omitted. Compared with the known accelerator 2,2-dithiobenzthiazole (Comparative Example 1) they possess the advantage that the rubber can be worked considerably more safely (measured as the scorch time t-s).

C: vulcanized rubbers with improved fatigue resistance and improved damping behaviour

Example 9

A tyre tread compound was prepared according to the procedure and composition used in Example 8, and was vulcanized for 20 minutes at 150° C. The cross-linking systems used were adjusted so that the vulcanized rubbers had the same density of cross-linking (measured as the modulus at 100% or 300% elongation):

| | |
|---|---|
| A: | 1.8 phr sulphur, 1.4 phr Example 1 |
| B: | 1.8 phr sulphur, 1.4 phr Example 2 |
| C: | 1.8 phr sulphur, 1.4 phr Example 6 |
| Comparison: | 1.2 phr sulphur, 1.4 phr morpholino-mercaptobenzthiazole sulphenamide (Vulkacit MOZ, Bayer) |

The fatigue resistance was determined by the Monsanto Fatigue-to-Failure test at 70° C., comprising the measurement of the number of elongations until fracture of the test piece occurred.

TABLE 2

| | A | B | C | Comparison |
|---|---|---|---|---|
| Strength (MPa) | 29 | 29 | 26 | 30 |
| Ultimate elongation (%) | 510 | 520 | 505 | 515 |
| Modulus 100 (MPa) | 2.3 | 2.2 | 2.0 | 2.2 |
| Modulus 300 (MPa) | 13.0 | 11.9 | 11.0 | 12.0 |
| Fatigue resistance (cycles × 100) | 475 | 770 | 980 | 265 |
| Tan delta (0° C.) | 0.209 | — | — | 0.195 |
| Tan delta (100° C.) | 0.086 | — | — | 0.108 |

It is clear that the dynamic fatigue resistance of the vulcanized rubbers with the new accelerators is significantly improved. Moreover, vulcanized rubber A according to the invention exhibits an increase in dynamic damping at 0° C. compared with accelerator tested for comparison (measured as tan delta in accordance with DIN 53513); according to the current state of knowledge, this is associated with an increased resistance to wet slippage. Reduced dynamic damping is also obtained at 100° C., which leads to a lower rolling resistance for motor vehicle tyres, as is known.

D: Activation of the filler in SBR vulcanized rubbers containing hydrated silica as the filler Example 10

Rubber compounds of the composition cited below were prepared in a kneader, at an internal temperature of 140° C. and a rotational speed of 50 rpm. The time of compounding was 5 minutes. Sulphur and accelerator were added at the end at 50° C. Test slabs 1 mm thick were then produced by vulcanization for 30 minutes at 160° C.

| Compound: | |
|---|---|
| Buna EM 1500 SBR rubber (HÜLS) | 70 pts. wt. |
| Buna EM 1778 SBR rubber (HÜLS) | 41 pts. wt. |
| Vulkasil S hydrated silica (BAYER) | 50 pts. wt. |
| Zinc oxide | 3 pts. wt. |
| Stearic acid | 2 pts. wt. |
| Diethylene glycol | 1.5 pts. wt. |
| Vulkanox OCD (BAYER) | 1 pt. wt. |
| Cumarone resin | 5 pts. wt. |
| Sulphur | 2 pts. wt. |
| Accelerator | 1.5 pts. wt. |

TABLE 3

| | Modulus 300 (MPa) | Strength (MPa) | Ultimate Elongation (%) |
|---|---|---|---|
| A: Compound from Ex. 1 | 3.8 | 17.5 | 1015 |
| B: Compound from Ex. 2 | 3.0 | 14.5 | 1080 |
| Comparison 1: | | | |
| Morpholino-mercapto-benzthiazole-sulphenamide | 1.9 | 10.5 | 1270 |

Comparison 2:
2-benzthiazolyl-dithiocyclohexane (Rubber Chem. Technol. 46 (5), 1299 to 1315): No vulcanization. Strong disagreeable odour.

The results verify that a higher density of cross-linking is obtained with the compounds according to the invention than with the sulphenamide accelerator of Comparison 1. This is due to an improved interaction of the polar groups, which are introduced into the rubber polymer chain by means of the accelerator, with the hydrated silica filler. The compounds used for comparison, which do not contain polar substituents (Comparisons 1 and 2) are not suitable at all for the vulcanization of this rubber compound. No test pieces could be produced. Moreover a disagreeable odour was produced, due to the liberation of mercaptans.

What is claimed is:

1. A vulcanizable rubber composition containing a vulcanization accelerator corresponding to the formula

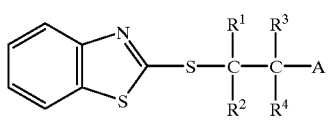

where A represents OH, OCOR$^5$, OR$^5$, COOR$^5$, NR$^6$R$^7$ or CN, wherein R$^5$, R$^6$ and R$^7$ are the same or different and represent hydrogen, or C$_1$–C$_{12}$ alkyl or C$_6$–C$_{10}$ aryl radicals, and R$^1$ to R$^4$ are the same or different and represent H, C$_1$–C$_{12}$ alkyl, C$_6$–C$_{10}$ aryl, CH$_2$OR$^5$, CH$_2$COOR$^5$ and CH$_2$OH.

2. A vulcanizable rubber composition containing a vulcanization accelerator selected from the group consisting of those having the following formulae;

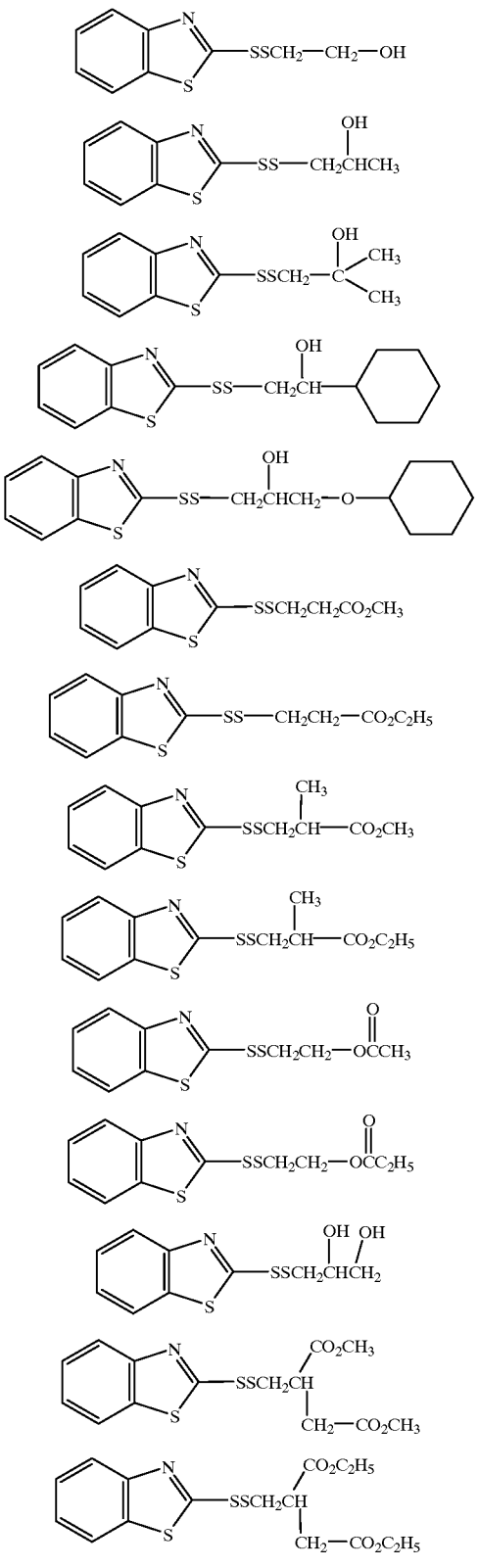

and

-continued

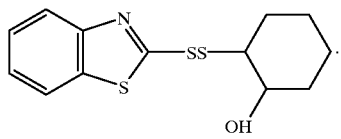

3. The composition of claim 1, wherein the vulcanization accelerator is present in on amount of 0.1 to 10% by weight, based on rubber in the composition.

4. The composition of claim 1, wherein the vulcanization accelerator is present in an amount of 0.3 to 4% by weight, based on rubber in the composition.

5. The composition of claim 2, wherein the vulcanization accelerator is present in an amount of 0.1 to 10% by weight, based on rubber in the composition.

6. The composition of claim 2, wherein the vulcanization accelerator is present in an amount of 0.3 to 4% by weight, based on rubber in the composition.

7. The composition of claim 1, wherein the rubber in the composition is one or more synthetic or natural rubbers.

8. The composition of claim 1 additionally containing a silicate filler.

* * * * *